United States Patent
Fredelake et al.

(10) Patent No.: US 9,474,901 B2
(45) Date of Patent: Oct. 25, 2016

(54) SYSTEM AND METHOD FOR NEURAL HEARING STIMULATION

(71) Applicant: Advanced Bionics AG, Stäfa (CH)

(72) Inventors: Stefan Fredelake, Oldenburg (DE); Waldo Nogueira, Hannover (DE)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 14/760,538

(22) PCT Filed: Jan. 11, 2013

(86) PCT No.: PCT/EP2013/050471
§ 371 (c)(1),
(2) Date: Jul. 13, 2015

(87) PCT Pub. No.: WO2014/108202
PCT Pub. Date: Jul. 17, 2014

(65) Prior Publication Data
US 2015/0352359 A1 Dec. 10, 2015

(51) Int. Cl.
*A61N 1/00* (2006.01)
*A61N 1/36* (2006.01)
*H04M 1/725* (2006.01)

(52) U.S. Cl.
CPC ...... *A61N 1/36032* (2013.01); *H04M 1/72591* (2013.01)

(58) Field of Classification Search
CPC .............. H04R 25/43; H04R 25/505; H04R 2205/041
See application file for complete search history.

(56) References Cited

U.S. PATENT DOCUMENTS

| 7,421,298 | B2 | 9/2008 | Daly et al. |
| 7,711,133 | B2 | 5/2010 | Goorevich et al. |
| 8,098,859 | B2 | 1/2012 | Zeng et al. |

(Continued)

FOREIGN PATENT DOCUMENTS

| EP | 2 375 782 A1 | 10/2011 |
| WO | 2008/154706 A1 | 12/2008 |
| WO | 2011/032021 A1 | 3/2011 |

OTHER PUBLICATIONS

Shinichi Sakamoto, Katsuhiko Goto, Makoto Tateno, Kimitaka Kaga, Frequency Compression Hearing Aid for Severe-To-Profound Hearing Impairments, Auris Nasus Larynx, vo. 27, No. 4, Oct. 1, 2000, p. 327-334.

*Primary Examiner* — Robert N Wieland
(74) *Attorney, Agent, or Firm* — David S. Safran

(57) ABSTRACT

An auditory prosthesis device for neural stimulation of a patient's hearing having an audio signal input device; a sound processor for generating a neural stimulation signal; and an implantable stimulation assembly having plural stimulation channels for stimulation of the patient's hearing, the sound processor having a filter bank for dividing the input audio signal into plural analysis channels, each containing a frequency domain signal representative of a portion of the audio signal, a signal level determiner for each analysis channel for analyzing the respective frequency domain signal, a neural stimulation signal generator for each analysis channel, a mapping unit for allocating the analysis channels to the stimulation channels according to an adjustable mapping scheme, and a control unit for controlling the mapping unit such that a standard mapping scheme is used in a standard operation mode and a low bandwidth mapping scheme is used in a low bandwidth operation mode.

31 Claims, 9 Drawing Sheets

(56) References Cited

U.S. PATENT DOCUMENTS

| | | |
|---|---|---|
| 8,422,706 B2 | 4/2013 | Kulkarni et al. |
| 8,605,923 B2 | 12/2013 | Goorevich et al. |
| 8,949,113 B2 | 2/2015 | Holmberg et al. |
| 2006/0052841 A1 | 3/2006 | Daly et al. |
| 2011/0019838 A1* | 1/2011 | Kaulberg ............ G10L 21/038 381/98 |
| 2012/0243715 A1* | 9/2012 | Pedersen ............ H04R 25/505 381/316 |
| 2013/0085549 A1* | 4/2013 | Case ............ H04R 25/43 607/55 |

* cited by examiner

SYSTEM AND METHOD FOR NEURAL HEARING STIMULATION

BACKGROUND OF THE INVENTION

1. Field of the Invention

The invention relates to a system and a method for neural stimulation of a patient's hearing, such as by cochlea stimulation.

2. Description of Related Art

The sense of hearing in human beings involves the use of hair cells in the cochlea that convert or transduce acoustic signals into auditory nerve impulses. Hearing loss, which may be due to many different causes, is generally of two types: conductive and sensori-neural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensori-neural hearing loss, on the other hand, is caused by the absence or destruction of the hair cells in the cochlea which are needed to transduce acoustic signals into auditory nerve impulses. People who suffer from sensori-neural hearing loss may be unable to derive significant benefit from conventional hearing aid systems, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensori-neural hearing loss, numerous auditory prosthesis systems (e.g., cochlear implant (CI) systems) have been developed. Auditory prosthesis systems bypass the hair cells in the cochlea by presenting electrical stimulation directly to the auditory nerve fibers. Direct stimulation of the auditory nerve fibers leads to the perception of sound in the brain and at least partial restoration of hearing function.

To facilitate direct stimulation of the auditory nerve fibers, a lead having an array of electrodes disposed thereon may be implanted in the cochlea of a patient. The electrodes form a number of stimulation channels through which electrical stimulation pulses may be applied directly to auditory nerves within the cochlea. An audio signal may then be presented to the patient by translating the audio signal into a number of electrical stimulation pulses and applying the stimulation pulses directly to the auditory nerve within the cochlea via one or more of the electrodes.

Typically, the audio signal, which usually is captured by a microphone, is divided into a plurality of analysis channels, each containing a frequency domain signal representative of a distinct frequency portion of the audio signal, wherein the frequency domain signal in each analysis channel may undergo signal processing, such as by applying channel-specific gain to the signals. The processed frequency domain signals are used for generating certain stimulation parameters according to which the stimulation signals in each stimulation channel is generated. The analysis channels are linked to the stimulation channels via channel mapping. The number of stimulation channels may correspond to the number of analysis channels, or there may be more stimulation channels than analysis channels, or there may be more analysis channels than stimulation channels. Various stimulation strategies are used, such as current steering stimulation (in order to stimulate a stimulation site located in between areas associated with two or more electrodes) and N-of-M stimulation (wherein stimulation current is only applied to N of M total stimulation channels during a particular stimulation frame).

An example for such a CI system with electrical cochlea stimulation is described in International Patent Application Publication WO 2011/032021 A1 and corresponding U.S. Pat. No. 8,422,706.

Patients, who are precluded from using a cochlear implant due to an illness or injury that has damaged the pateint's cochlea or auditory nerve, may be provided with an auditory brainstem implant or an auditory midbrain implant. Such devices use similar technology as a cochlear implant, but instead of electrical stimulation being used to stimulate the cochlea, it is used to stimulate the brainstem or midbrain of the recipient.

With CI systems, speech intelligibility is restored at a great inter-individual variability, i.e., some CI patients achieve open speech intelligibility, whereas other CI patients are not able to understand speech without visual assistance, such as lip reading or sign language. In particular, speech perception is difficult for many auditory prosthesis users when using a phone, since audio signal bandwidth of telephone systems is limited to a frequency range of about 300 to 3400 Hz, while speech audio signals have a frequency range of about 100 to 8000 Hz. While normal hearing persons usually are able to understand such band limited speech, hearing impaired persons often have problems.

An established approach for enhancing speech intelligibility during phone use of hearing impaired persons is to provide the hearing device with a telecoil (T-coil) which records the inductive audio signal produced by the loudspeaker of the telephone device and presents this audio signal as input to the hearing device, whereby an enhanced signal to noise ratio can be achieved.

Due to the limited spectral resolution of neural stimulation auditory prosthesis devices, such as CI systems, auditory brain stem implants or auditory mid-brain implants, reduced speech intelligibility due to bandwidth limitation of the input audio signal, such as present in a telephone audio signal, is particularly severe.

The article "A Phone-Assistive Device Based on Bluetooth Technology for Cochlea Implant Users" by H. Qian et al., IEEE Transactions on Neural Systems and Rehabilitation Engineering, 2003, pages 282 to 287, proposes a wireless phone adapter based on Bluetooth technology which can be used to route the audio signal from a telephone device directly to a hearing aid or CI processor.

The article "Frequency-to-electrode allocation and speech reception with cochlear implants" by C. McKay et al., J. Acoust. Soc. Am. 111 (2), 2002, pages 1036 to 1044, relates to speech recognition tests on CI systems, wherein the frequency-to-electrode allocation was varied.

The article "The effect of short-term training for spectrally mismatched noise-band speech" by Q.-J. Fu et al., J. Acoust. Soc. Am. 113 (2), 2003, pages 1065 to 1072, relates to a study wherein acoustic information was spectrally distorted by shifting speech information from one frequency region to another, with the audio signals being presented to normal hearing persons.

The article "Frequency-place compression and expansion in cochlear implant listeners", D. Baskent et al., J. Acoust. Soc. Am. 116 (5), 2004, pages 3130 to 3140, relates to a study wherein effects of frequency-place compression and expansion on speech perception by CI users were investigated.

European Patent Application EP 2 375 782 A1 and corresponding U.S. Pat. No. 8,949,113 relate to a signal processing in instruments, wherein it is mentioned that frequency compression or expansion may be used for reducing bandwidth requirements for an audio transmission channel such as a telephone standard channel.

U.S. Pat. No. 8,098,859 B2 relates to a CI system comprising a frequency upward-shifting processor and a formant upward-shifting processor for shifting low frequency audio signals into a higher frequency range, with such system being applicable to patients suffering from low frequency hearing loss.

International Patent Application Publication WO 2008/154706 A1 and corresponding U.S. Pat. No. 8,605,923 relate to a CI system having several audio signal processing modes which are selected according to the result of an auditory scheme analysis.

U.S. Pat. No. 7,711,133 B2 relates to a CI system wherein the frequency resolution of the filter bank is higher for certain frequency ranges, such as the frequencies most relevant for speech recognition.

SUMMARY OF THE INVENTION

It is an object of the invention to provide for a neural stimulation auditory prosthesis device which provides for good speech perception for band limited input audio signals. It is a further object to provide for a corresponding neural stimulation method.

According to the invention, these objects are achieved by auditory prosthesis devices and neural stimulation methods as described herein.

The invention is beneficial in that, by providing the sound processor with an adjustable mapping unit and/or an adjustable filter bank, with the mapping scheme and/or the filter bank settings being changed with regard to the setting in the standard operation mode of the device when the device is in a low bandwidth operation mode, the mapping scheme and/or the filter bank settings can be adjusted when the input audio signal has a lower bandwidth than in normal operation, such as when using a phone, in such a manner that speech perception of such low bandwidth signals can be enhanced.

In order to change between the standard operation mode and the low bandwidth operation mode the device may be provided with a manually operable switch. Alternatively, or in addition, the sound processor may comprise a classifier unit in order to determine whether the present input audio signal qualifies as a low bandwidth input audio signal, so that the device can automatically change from a standard operation mode to the low bandwidth operation mode.

Hereinafter, examples of the invention will be illustrated by reference to the accompanying drawings.

DETAILED DESCRIPTION OF THE INVENTION

Figure 1:
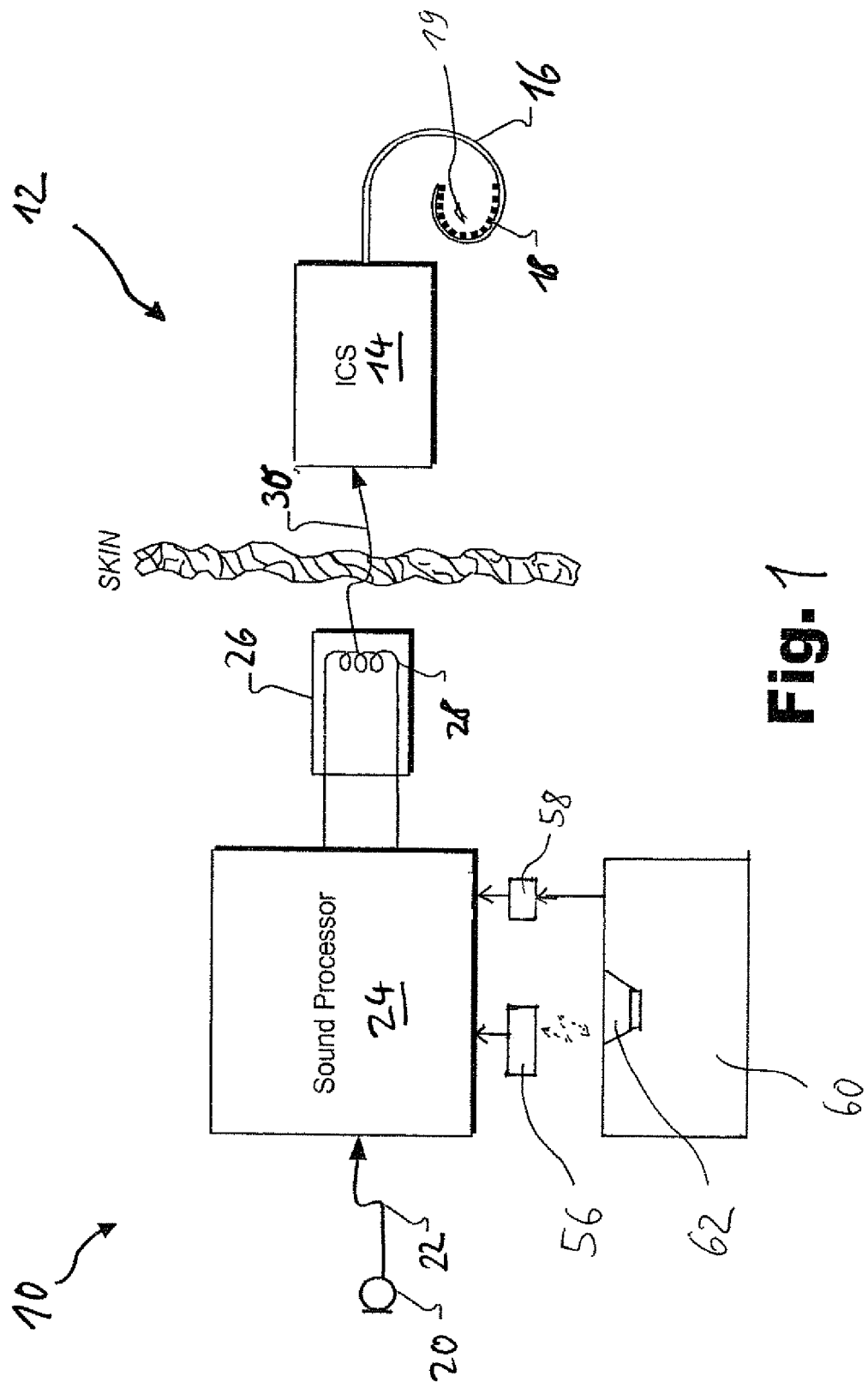
FIG. 1 is a schematic view of an example of a CI system according to the invention.

In FIG. 1, an example of a cochlear implant system is shown schematically. The system comprises a sound processing sub-system 10 and a stimulation sub-system 12. The sound processing sub-system 10 serves to detect or sense an audio signal and divide the audio signal into a plurality of analysis channels each containing a frequency domain signal (or simply "signal") representative of a distinct frequency portion of the audio signal. A signal level value and a noise level value are determined for each analysis channel by analyzing the respective frequency domain signal, and a noise reduction gain parameter is determined for each analysis channel as a function of the signal level value and the noise level value of the respective analysis channel. Noise reduction is applied to the frequency domain signal according to the noise reduction gain parameters to generate a noise reduced frequency domain signal. Stimulation parameters are generated based on the noise reduced frequency domain signal and are transmitted to the stimulation sub-system 12.

Stimulation sub-system 12 serves to generate and apply electrical stimulation (also referred to herein as "stimulation current" and/or "stimulation pulses") to stimulation sites at the auditory nerve within the cochlear of a patient in accordance with the stimulation parameters received from the sound processing sub-system 10. Electrical stimulation is provided to the patient via a CI stimulation assembly 18 comprising a plurality of stimulation channels, wherein various known stimulation strategies, such as current steering stimulation or N-of-M stimulation, may be utilized.

As used herein, a "current steering stimulation strategy" is one in which weighted stimulation current is applied concurrently to two or more electrodes by an implantable cochlear stimulator in order to stimulate a stimulation site located in between areas associated with the two or more electrodes and thereby create a perception of a frequency in between the frequencies associated with the two or more electrodes, compensate for one or more disabled electrodes, and/or generate a target pitch that is outside a range of pitches associated with an array of electrodes.

As used herein, an "N-of-M stimulation strategy" is one in which stimulation current is only applied to N of M total stimulation channels during a particular stimulation frame, where N is less than M. An N-of-M stimulation strategy may be used to prevent irrelevant information contained within an audio signal from being presented to a CI user, achieve higher stimulation rates, minimize electrode interaction, and/or for any other reason as may serve a particular application.

The stimulation parameters may control various parameters of the electrical stimulation applied to a stimulation site including, but not limited to, frequency, pulse width, amplitude, waveform (e.g., square or sinusoidal), electrode polarity (i.e., anode-cathode assignment), location (i.e., which electrode pair or electrode group receives the stimulation current), burst pattern (e.g., burst on time and burst off time), duty cycle or burst repeat interval, spectral tilt, ramp on time, and ramp off time of the stimulation current that is applied to the stimulation site.

Figure 2:
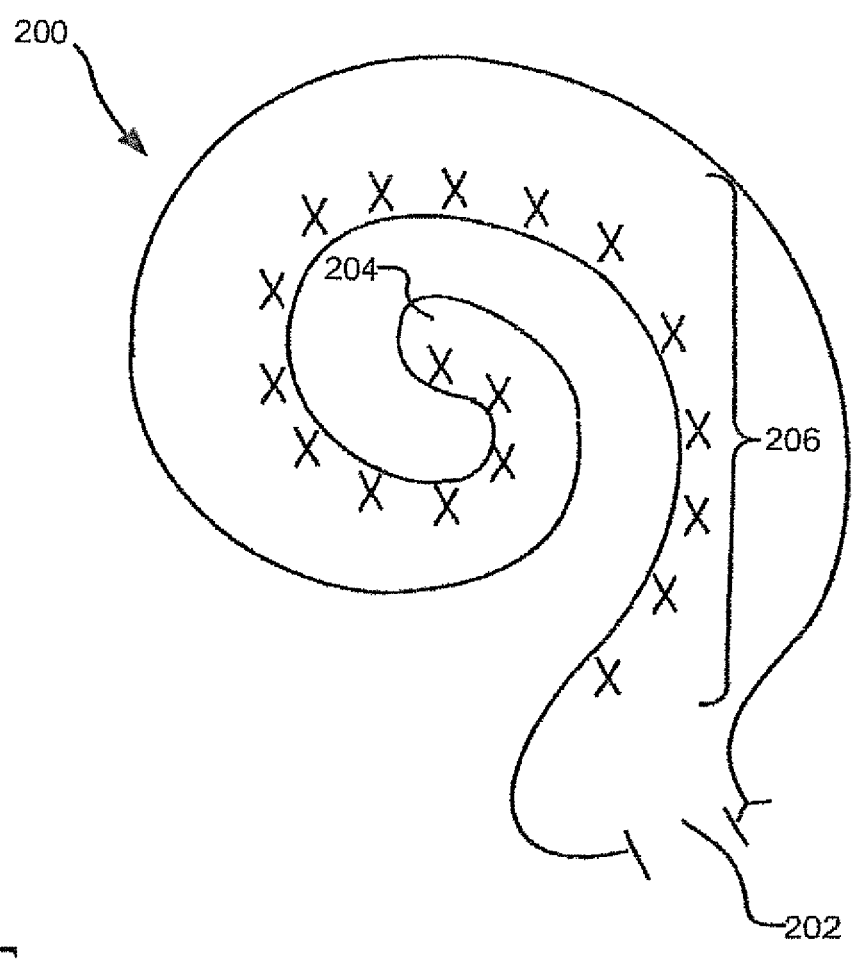
FIG. 2 is a schematic cross-sectional view of a human cochlea with marked stimulation sites.

FIG. 2 illustrates a schematic structure of the human cochlea 200. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Low frequencies are encoded at the apex 204 of the cochlea 200 while high frequencies are encoded at the base 202. Hence, each location along the length of the cochlea 200 corresponds to a different perceived frequency. Stimulation subsystem 12 is configured to apply stimulation to different locations within the cochlea 200 (e.g., different locations along the auditory nerve tissue 206) to provide a sensation of hearing.

Returning to FIG. 1, sound processing subsystem 10 and stimulation subsystem 12 may be configured to operate in accordance with one or more control parameters. These control parameters may be configured to specify one or more stimulation parameters, operating parameters, and/or any other parameter as may serve a particular application. Exemplary control parameters include, but are not limited to, most comfortable current levels ("M levels"), threshold current levels ("T levels"), dynamic range parameters, channel acoustic gain parameters, front and backend dynamic range parameters, current steering parameters, amplitude values, pulse rate values, pulse width values, polarity values, filter characteristics, and/or any other control parameter as may serve a particular application.

In the example shown in FIG. 1, the stimulation subsystem 12 comprises an implantable cochlear stimulator ("ICS") 14, a lead 16 and the stimulation assembly 18 disposed on the lead 16. The stimulation assembly 18 comprises a plurality of "stimulation contacts" 19 for electrical stimulation of the auditory nerve. The lead 16 may be inserted within a duct of the cochlea in such a manner that the stimulation contacts 19 are in communication with one or more stimulation sites within the cochlea, i.e., the stimulation contacts 19 are adjacent to, in the general vicinity of, in close proximity to, directly next to, or directly on the respective stimulation site.

In the example shown in FIG. 1, the sound processing sub-system 10 is designed to be located external to the patient; however, in alternative examples, at least one of the components of the sub-system 10 may be implantable.

In the example shown in FIG. 1, the sound processing sub-system 10 comprises a microphone 20 which captures audio signals from ambient sound, a microphone link 22, a sound processor 24 which receives audio signals from the microphone 20 via the link 22, and a headpiece 26 having a coil 28 disposed therein. The sound processor 24 is configured to process the captured audio signals in accordance with a selected sound processing strategy to generate appropriate stimulation parameters for controlling the ICS 14 and may include, or be implemented within, a behind-the-ear (BTE) unit or a portable speech processor ("PSP"). In the example of FIG. 1 the sound processor 24 is configured to transcutaneously transmit data (in particular data representative of one or more stimulation parameters) to the ICS 14 via a wireless transcutaneous communication link 30. The headpiece 26 may be affixed to the patient's head and positioned such that the coil 28 is communicatively coupled to the corresponding coil (not shown) included within the ICS 14 in order to establish the link 30. The link 30 may include a bidirectional communication link and/or one or more dedicated unidirectional communication links. According to an alternative embodiment, the sound processor 24 and the ICS 14 may be directly connected by wires.

Figure 3:
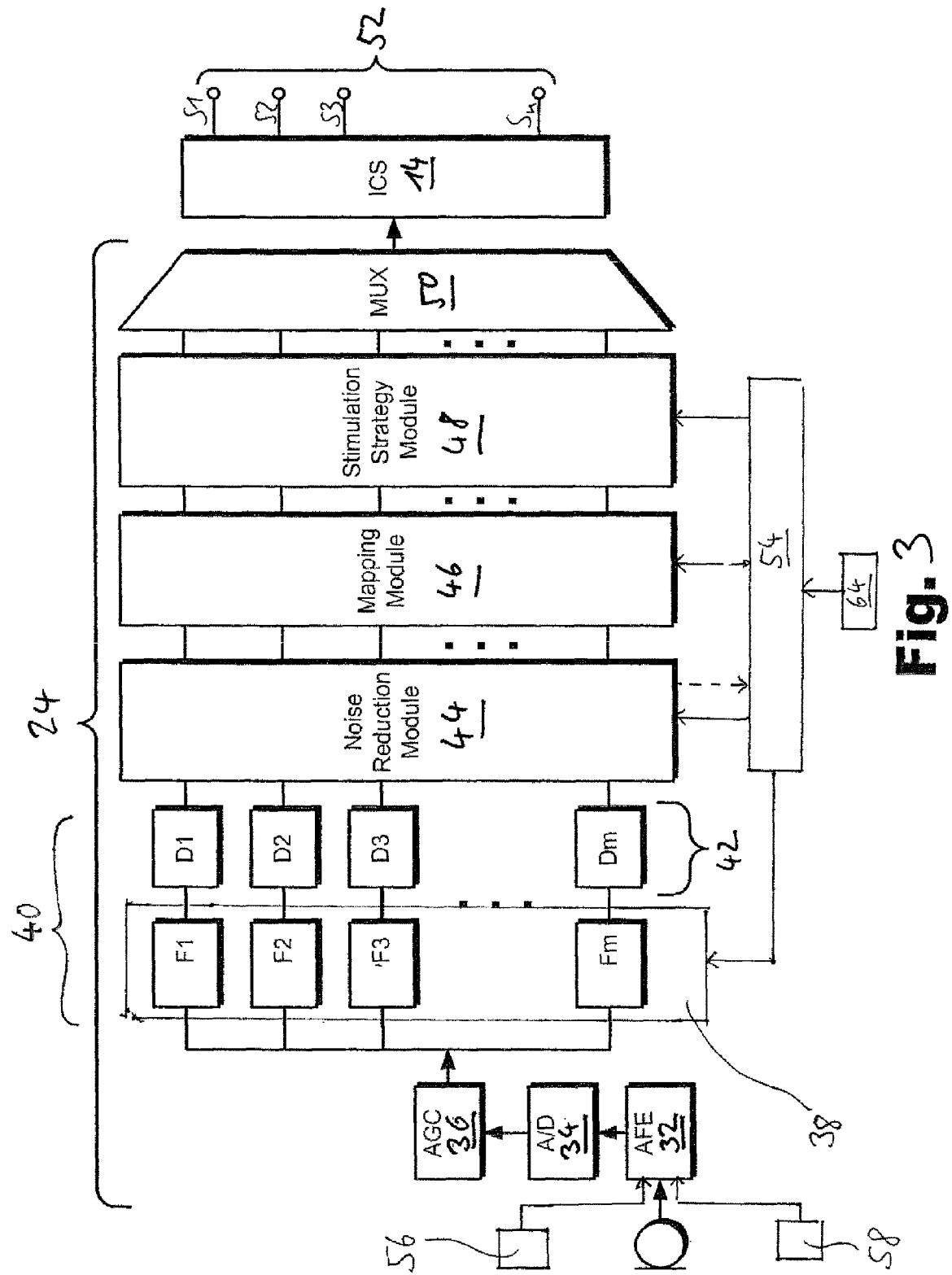
FIG. 3 is a block diagram of the signal processing structure of a CI system according to the invention.

In FIG. 3, a schematic example of a sound processor 24 is shown. The audio signals captured by the microphone 20 are amplified in an audio front end circuitry 32, with the amplified audio signal being converted to a digital signal by an analog-to-digital converter 34. The resulting digital signal is then subjected to automatic gain control using a suitable automatic gain control (AGC) unit 36.

After appropriate automatic gain control, the digital signal is subjected to a filter bank 38 comprising a plurality of filters F1 . . . Fm (for example, band-pass filters) which are configured to divide the digital signal into m analysis channels 40, each containing a signal representative of a distinct frequency portion of the audio signal sensed by the microphone 20. For example, such frequency filtering may be implemented by applying a Discrete Fourier Transform to the audio signal and then divide the resulting frequency bins into the analysis channels 40.

The signals within each analysis channel 40 are input into an envelope detector 42 in order to determine the amount of energy contained within each of the signals within the analysis channels 40 and to estimate the noise within each channel. After envelope detection the signals within the analysis channels 40 are input into a noise reduction module 44, wherein the signals are treated in a manner so as to reduce noise in the signal in order to enhance, for example, the intelligibility of speech by the patient. Examples of the noise reduction module 44 are described e.g., in International Patent Application Publication WO 2011/032021 A1 and corresponding U.S. Pat. No. 8,422,706.

The noise reduced signals are supplied to a mapping module 46 which serves to map the signals in the analysis channels 40 to the stimulation channels S1 . . . Sn. For example, signal levels of the noise reduced signals may be mapped to amplitude values used to define the electrical stimulation pulses that are applied to the patient by the ICS 14 via M stimulation channels 52. For example, each of the m stimulation channels 52 may be associated to one of the stimulation contacts 19 or to a group of the stimulation contacts 19. Such mapping concerns both amplitude mapping, the acoustic sound level in an analysis channel is mapped to an electric amplitude in the stimulation channel (e.g. to a certain stimulation current level), and allocation of a certain frequency range to a certain stimulation site/electrode (i.e., allocation of a certain analysis channel to a certain stimulation channel). Both kinds of mapping can be effected by the same mapping module 46 or by separate mapping modules (not shown).

Further, the mapping may take place after the noise reduction (as shown in FIG. 3), or it may take place prior to noise reduction (not shown).

The sound processor 24 further comprises a stimulation strategy module 48 which serves to generate one or more stimulation parameters based on the noise reduced signals and in accordance with a certain stimulation strategy (which may be selected from a plurality of stimulation strategies). For example, stimulation strategy module 48 may generate stimulation parameters which direct the ICS 14 to generate and concurrently apply weighted stimulation current via a plurality 52 of the stimulation channels S1 . . . Sn in order to effectuate a current steering stimulation strategy. Additionally or alternatively the stimulation strategy module 48 may be configured to generate stimulation parameters which direct the ICS 14 to apply electrical stimulation via only a subset N of the stimulation channels 52 in order to effectuate an N-of-M stimulation strategy.

The sound processor 24 also comprises a multiplexer 50 which serves to serialize the stimulation parameters generated by the stimulation strategy module 48 so that they can be transmitted to the ICS 14 via the communication link 30, i.e., via the coil 28.

The sound processor 24 may operate in accordance with at least one control parameter which is set by a control unit 54. Such control parameters may be the most comfortable listening current levels (MCL), also referred to as "M levels", threshold current levels (also referred to as "T levels"), dynamic range parameters, channel acoustic gain parameters, front and back end dynamic range parameters, AGC parameters, current steering parameters, amplitude values, pulse rate values, pulse width values, polarity values and/or filter characteristics. Examples of such auditory prosthesis devices, as described so far, can be found, for example, in WO 2011/032021 A1 and corresponding U.S. Pat. No. 8,422,706.

The sound processor 24 may be provided not only with a microphone input but also with a T-coil 56 and/or with an interface 58 for wired connection to external audio devices, such as a phone device 60. The T-coil 56 is for inductive coupling with the driver of the loudspeaker 62 of the phone device 60 in order to supply the audio signals generated by the phone device 60 directly, i.e., without using the microphone 20, to the sound processor 24. However, alternatively, audio signals may be supplied from the phone device 60 to the sound processor 24 acoustically, i.e., via the speaker 62 and the microphone 20. Alternatively or in addition, the audio signals from the phone device 60 may be supplied via the wired interface 58 to the sound processor 24. As an alternative to the T-coil 56, the audio signals may be supplied from the phone device 60 via a wireless interface, such as a Bluetooth interface (in this the wireless interface would be represented by the element 56, and the respective link would be represented at 59.

In any case, the audio signals supplied to the sound processor 24 from the phone device 60 will have a limited bandwidth corresponding to the limited bandwidth of telecommunication systems. As already mentioned above, typically telephone audio signals are limited to a frequency range of about 300 to 3400 Hz.

The filter bank 38 and/or the mapping module 46 are adjustable and are controlled by the control unit 54 in such a manner that the respective settings are different depending on whether a "normal" audio signal having no bandwidth limitation (such as speech captured by the microphone 22 from a person speaking to the CI user) or a bandwidth limited audio signal (such as an audio signal originating from a telephone device) is supplied to the sound processor 24. In other words, the control unit 54 determines whether the sound processor 24 is operated in a standard operation mode or in a low bandwidth operation mode. In the standard operation mode, the mapping module 46 uses a standard mapping scheme, whereas it uses a low bandwidth mapping scheme in the low bandwidth operation mode; similarly, the filter bank 38 uses a standard filter bank setting in the standard operation mode, whereas it uses a low bandwidth filter bank setting in the low bandwidth operation mode.

A manually operable switch 64 may be provided for causing the control unit 54 to change between the standard operation mode and the low bandwidth operation mode and vice versa. Such switch 64, for example, may be operated by the CI user when he starts to use the phone device 60 and when he finishes using the phone device 60. Alternatively or in addition, the sound processor 24 may be provided with a classifier unit for determining automatically whether the input audio signal qualifies as a low bandwidth input audio signal in order to cause the control unit 54 to switch from the standard operation mode to the low bandwidth operation mode and vice versa. For example, the classifier may form part of the noise reduction module 44 and provides a corresponding status signal to the control unit 54. However, a classifier is not needed, if adaptive filters are used for adapting to the low bandwidth mode.

Figure 4:
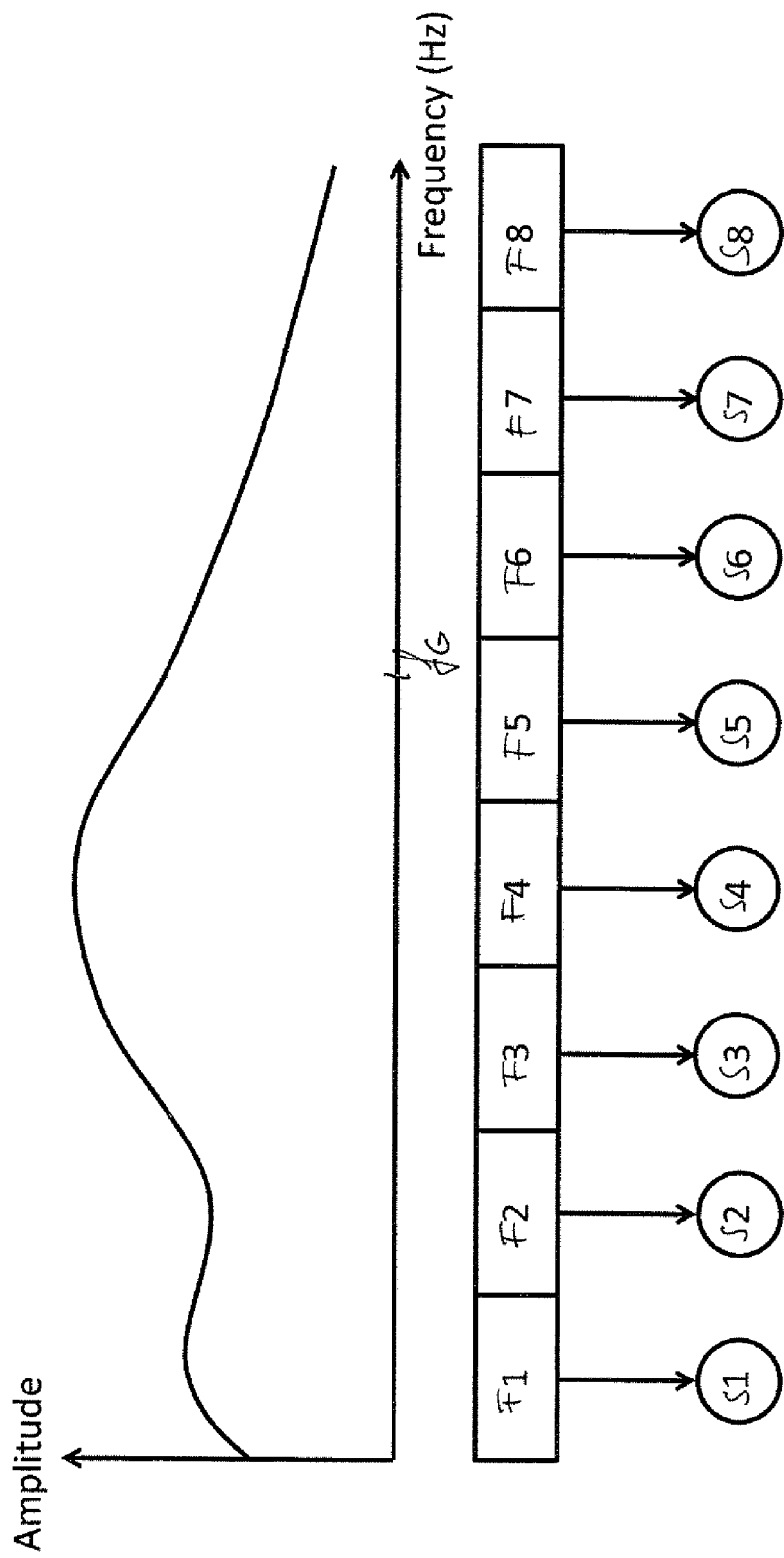
FIG. 4 is a schematic example of the frequency-to-electrode mapping of a CI system in a standard operation mode.
Figure 5:
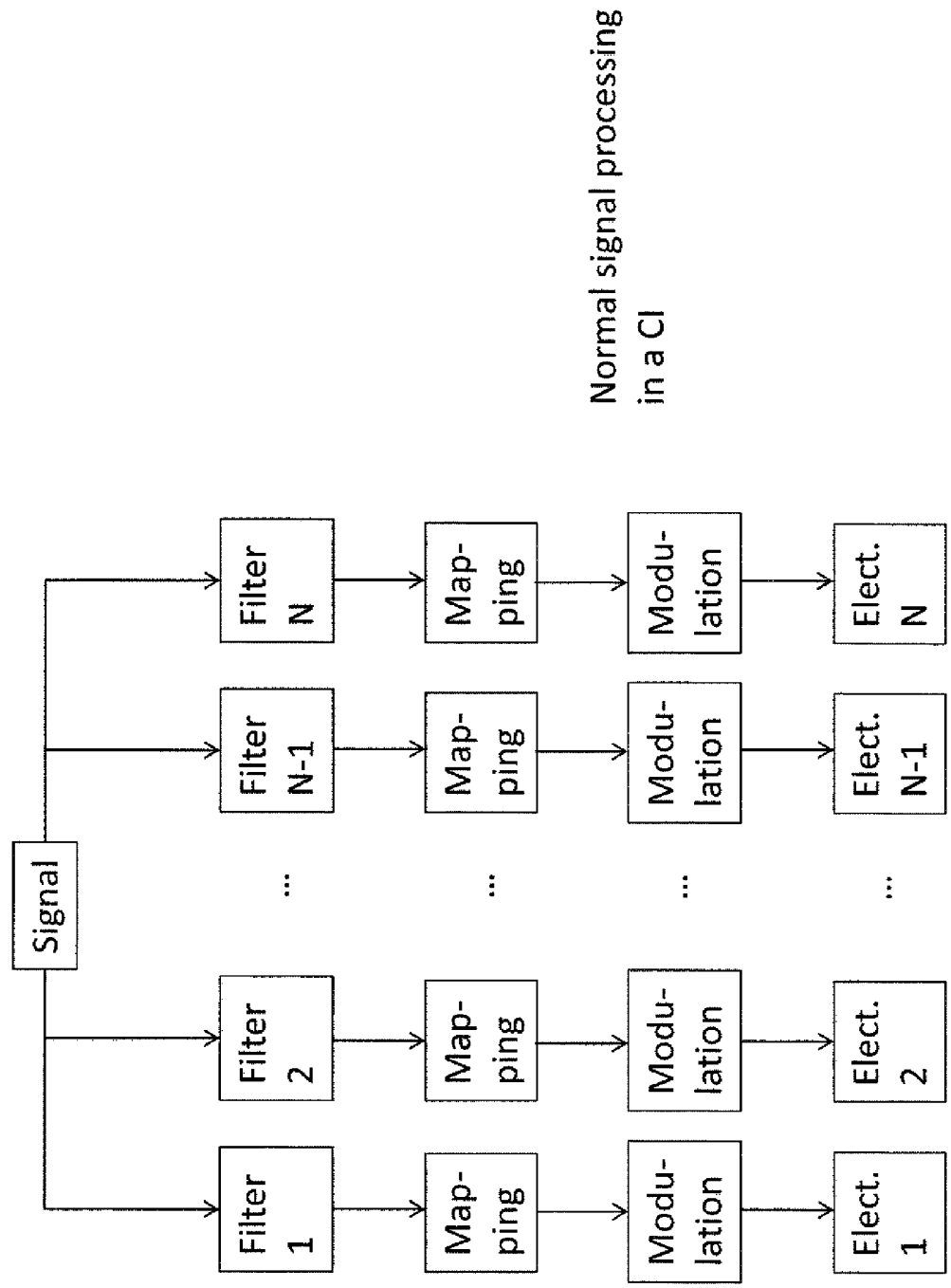
FIG. 5 is a block diagram of the signal processing in the standard operation mode illustrated in FIG. 4.

A schematic example of the setting of the filter bank 38 and of the mapping scheme in the standard operation mode is shown in FIGS. 4 & 5, according to which each of the filters F1, F2, . . . representing one of the analysis channels is mapped to a different one of the electrodes S1, S2, . . . , respectively, representing the stimulation channels. In this case, the spectrum of the input audio signal covers the entire range of the filter bank 38, resulting in stimulation of all electrodes S1, S2, . . . according to the respective signal level in the respective analysis channel F1, F2, . . . .

Figure 6:
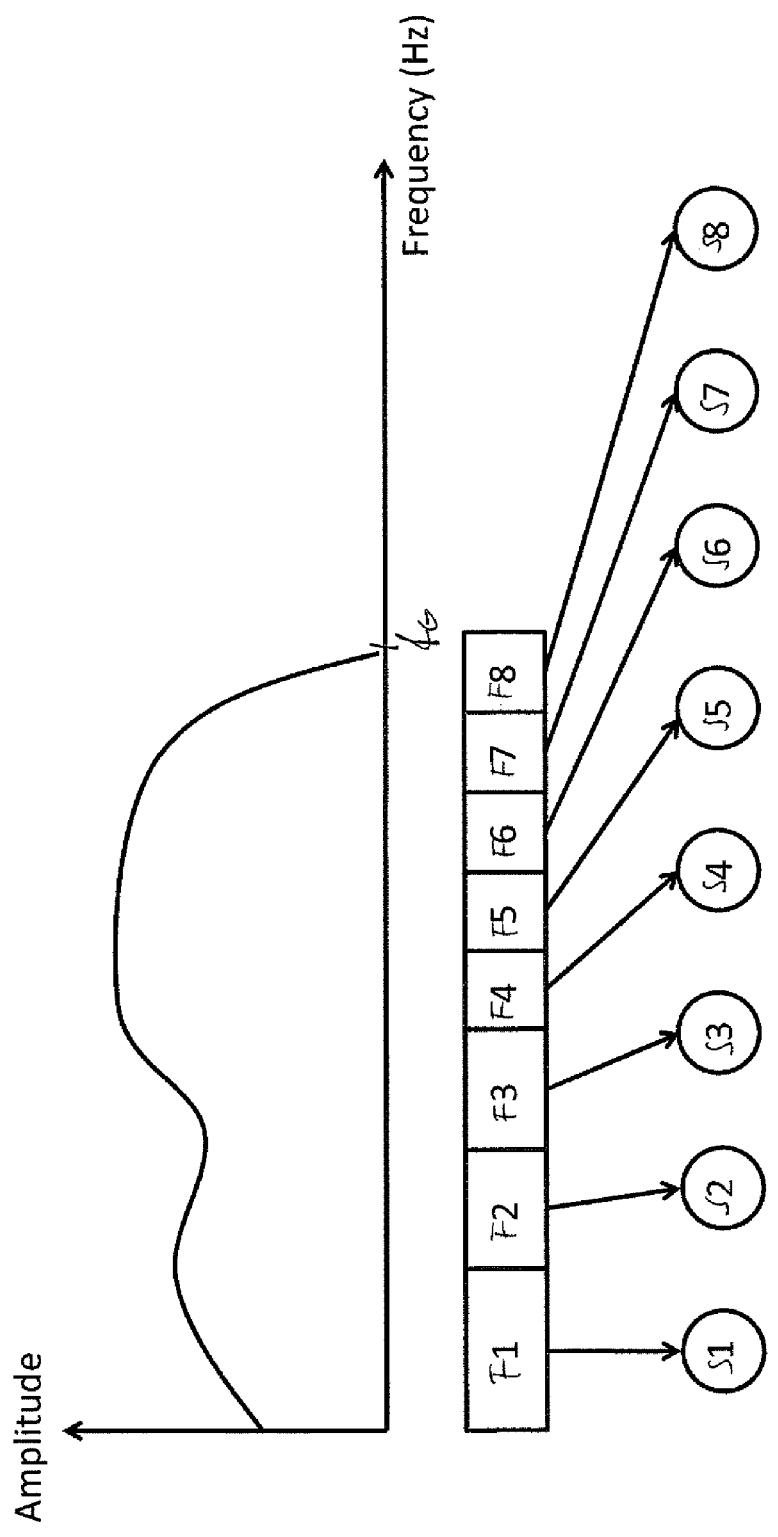
FIGS. 6 and 7 show a schematic example of the change of the filter bank setting when the CI system is in a low bandwidth operation mode, wherein the mapping scheme is shown in FIG. 6 and the signal processing is shown in FIG. 7.
Figure 7:
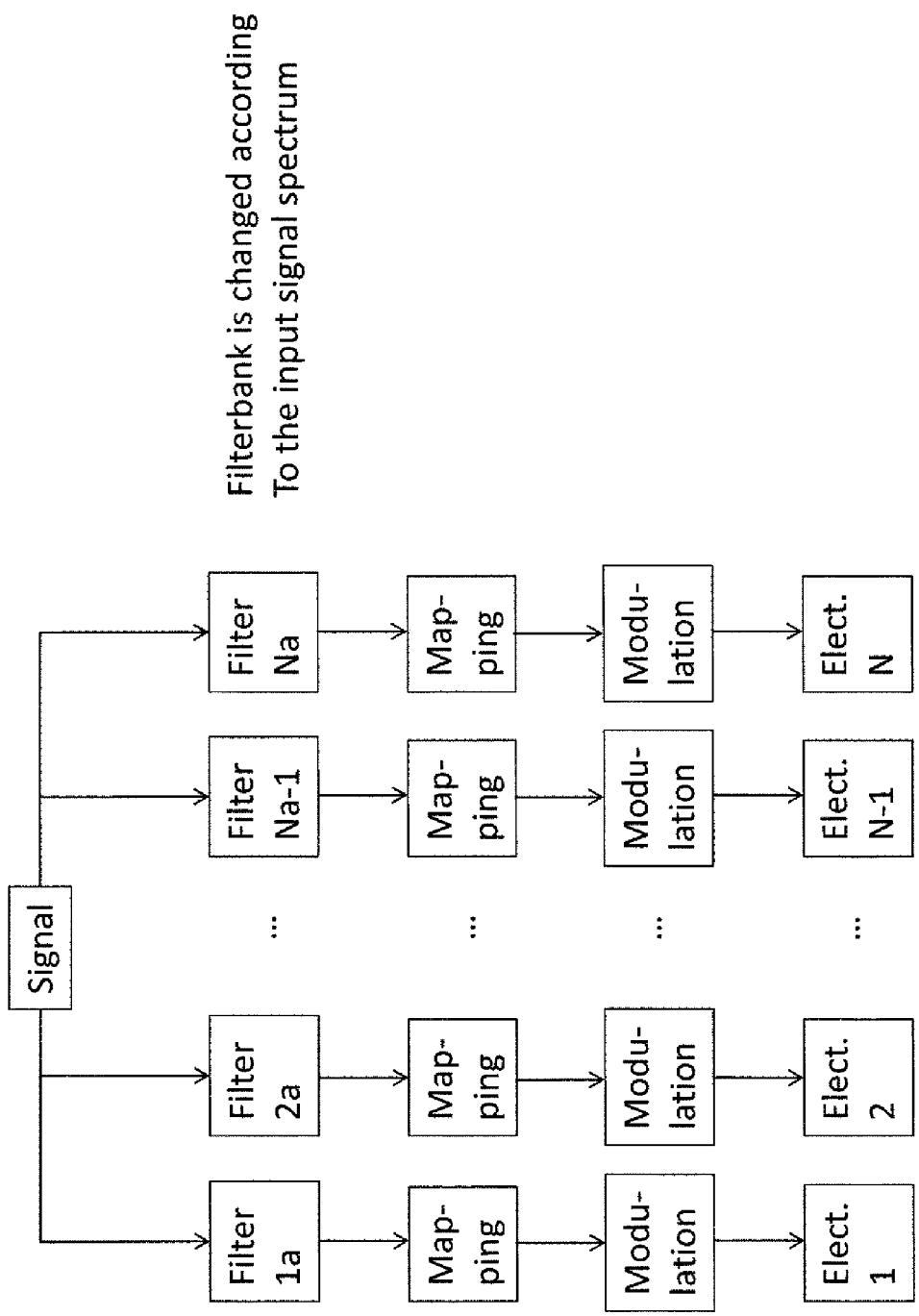

In FIGS. 6 & 7, a first schematic example of an input audio signal, the filter bank setting and the mapping scheme in the low bandwidth operation mode is shown. In this case, the input audio signal does not contain frequencies above a certain upper limit $f_G$ (in case of a telephone audio signal, this upper limit may be for example 3400 Hz). In the example of FIGS. 6 & 7, the filter bank 38 is "compressed" (i.e., adapted) towards lower frequencies with regard to the standard filter bank setting by lowering the center frequency and the width of at least some of the analysis channels F1, F2, . . . . Typically, the center frequency of each analysis is lowered the more the higher the center frequency of the respective analysis channel in the standard filter bank setting is. Preferably, the filter bank 38 is "compressed" (or adapted) to such an extent that the analysis channel having the highest frequency (i.e., the filter F8 in FIG. 6) is located at the upper limit $f_G$ of the input audio signal spectrum.

However, it also may be conceivable in some cases to compress/adapt the filter bank 38 towards higher frequencies.

In the example of FIGS. 6 & 7, the mapping scheme remains unchanged in the low bandwidth operation mode, i.e., each analysis channel F1, F2, . . . is mapped to the same stimulation channel S1, S2, . . . as in the standard operation mode.

Figure 8:
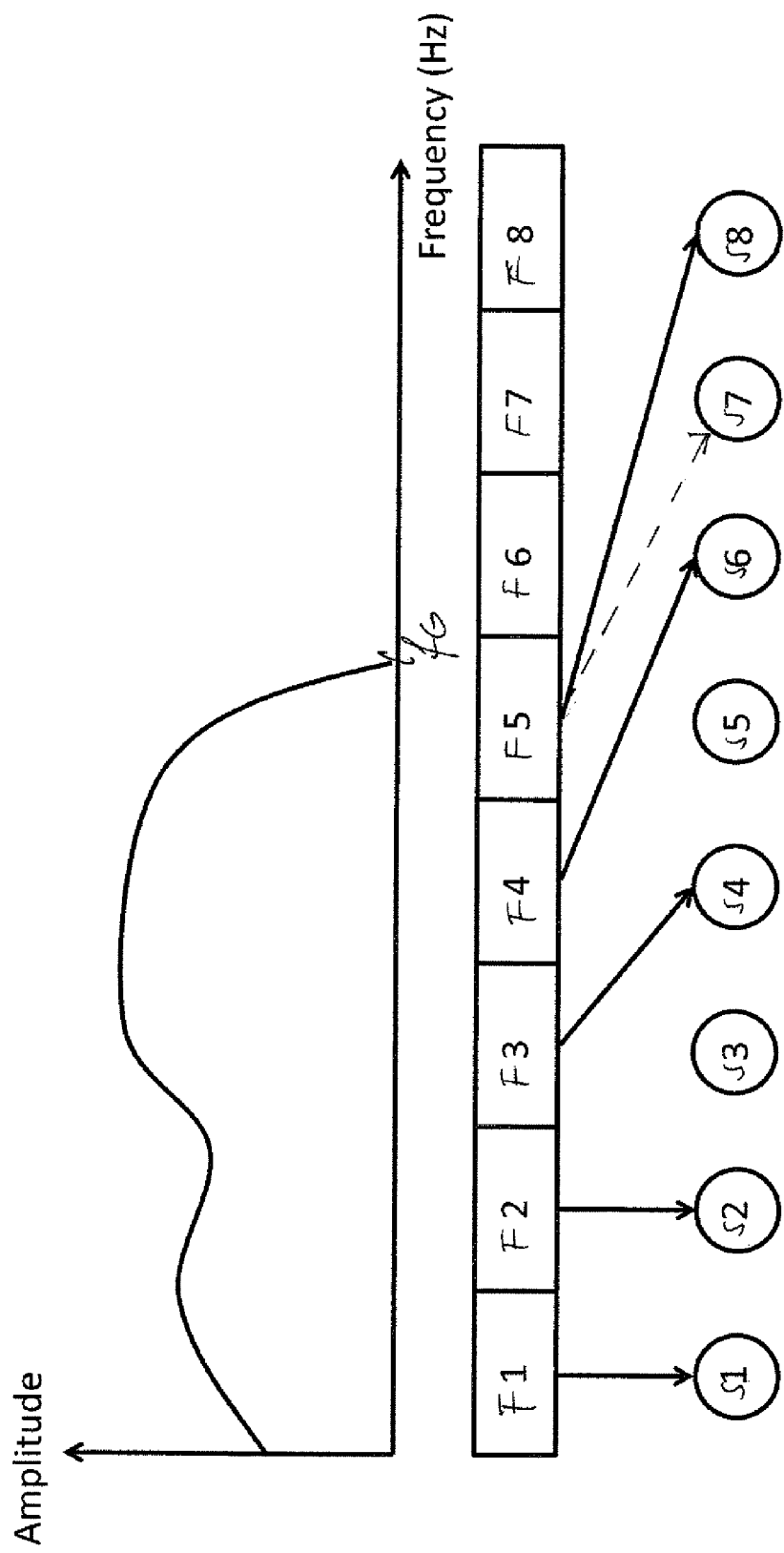
FIGS. 8 and 9 show an alternative example of the mapping and signal processing in the low bandwidth operation mode, wherein the filter bank settings are the same as in the standard operation mode, but wherein the mapping scheme is changed.
Figure 9:
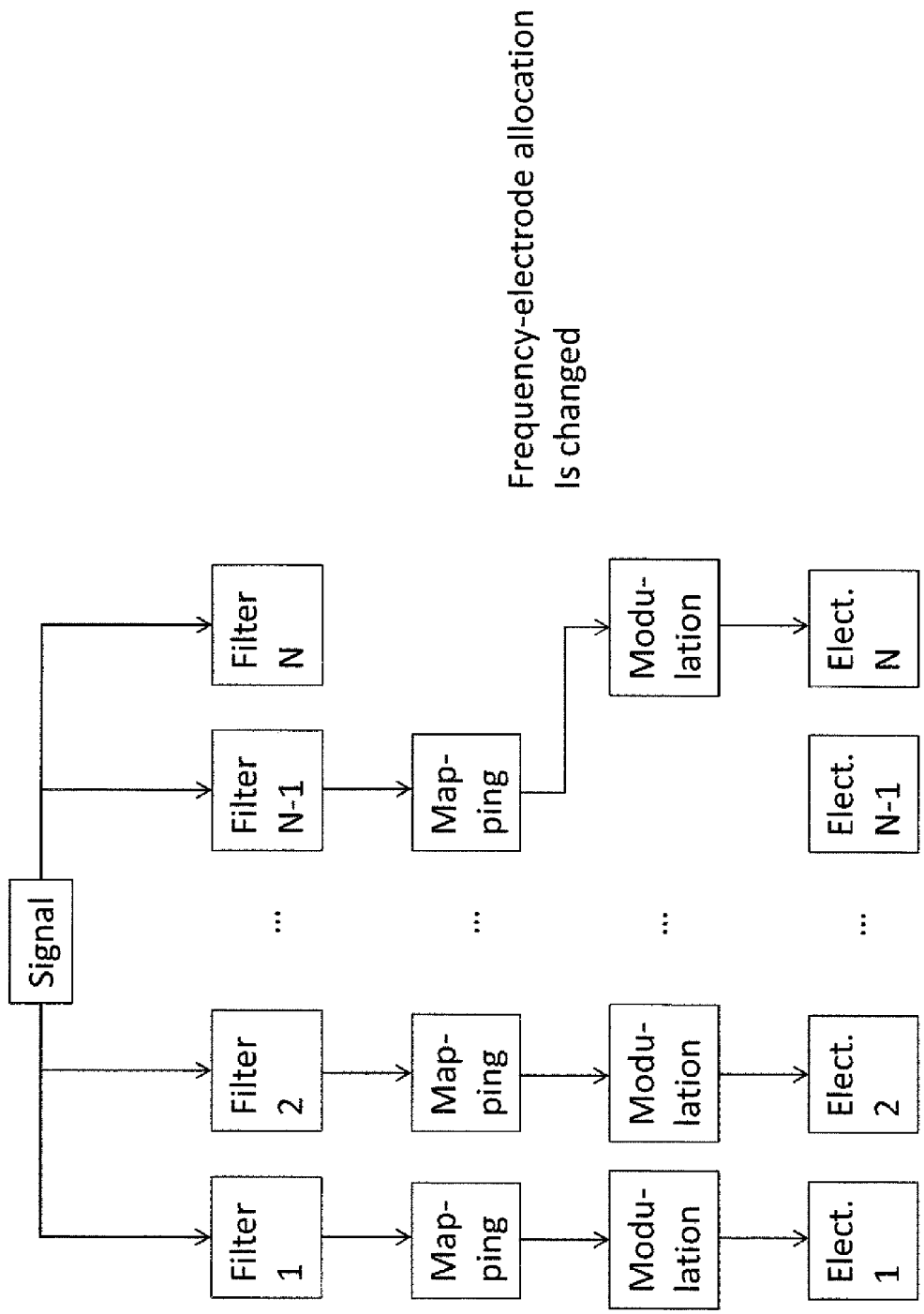

An alternative schematic example of the filter bank setting and the mapping scheme in the low bandwidth operation mode is shown in FIGS. 8 & 9. In this case, the filter bank setting remains unchanged with regard to the standard operation mode, whereas the mapping scheme is changed. Typically, at least one of the analysis channels is mapped to a stimulation channel corresponding to higher frequency stimulation than the stimulation channel it is mapped to in the standard mapping scheme (in the case of a CI, the position of the respective electrode determines whether stimulation by the stimulation channel attributed to that electrode is perceived as a low frequency hearing perception or as a high frequency hearing perception, see FIG. 2). However, it also may be possible in some cases to map at least one of the analysis channels to a lower to a stimulation channel corresponding to lower frequency stimulation than the stimulation channel it is mapped to in the standard mapping scheme. For example, if the first electrode S1 is allocated to 120 Hz in the standard mode, then for telephone speech, low frequencies (e.g. below 300 Hz) could also be mapped to the first electrode S1.

In the example shown in FIG. 8, the analysis channels F3, F4 and F5 are mapped to electrodes S4, S6 and S8 which correspond to higher frequency stimulation than the electrode (S3, S5 and S7, respectively) to which the respective analysis channel is mapped to in the standard operation mode. Typically, the stimulation channels having a center frequency above a first threshold frequency but below the upper limit $f_G$ of the input audio signal spectrum are mapped to a stimulation channel corresponding to higher frequency stimulation than the stimulation channel the analysis channel is mapped to in the standard mapping scheme; in the example of FIG. 8, this condition is fulfilled for the analysis channels F3, F4 and F5. Typically, the analysis channels having a center frequency above the upper limit $f_G$ of the input audio signal spectrum are no longer mapped to a stimulation channel in the low bandwidth mode (in the example of FIG. 8, this condition is fulfilled for the analysis channels F6, F7 and F8).

According to the mapping scheme of FIG. 8, the stimulation channels S3, S5 and S7 are no longer mapped to an analysis channel and therefore do not contribute to stimulation caused by the input audio signal. For the analysis channels having the lowest center frequencies the mapping scheme may be the same as in the standard operation mode (in the example of FIG. 8, this applies to the analysis channels F1 and F2).

Stimulation channels which are not mapped to an analysis channel in the low bandwidth operation mode may be used for applying a stimulation signal which is generated from an artificial signal reconstructed from the input audio signal, which artificial signal consists of frequencies outside the bandwidth of the input audio signal. In other words, the information contained in the bandwidth limited audio signal may be used for stimulation of the hearing outside the limited frequency range to some extent. For example, higher harmonics lying outside the audio signal spectrum may be reconstructed from the harmonics contained within the audio signal spectrum. Such signal reconstruction is particularly useful for the stimulation channels corresponding to the highest frequencies. For example, in the example of FIG. 8, if the analysis channel F5 were allocated to the stimulation channel S7 rather than to S8 (see dashed line), the electrode S8 could be used for stimulation according to such a reconstructed signal.

In principle, the approaches of FIG. 6 and FIG. 8 may be combined, i.e., in the low bandwidth operation mode both the filter bank setting and the mapping scheme could be changed with regard to the standard operation mode.

The upper limit $f_G$ could be implemented as a fixed value, but it also could be derived from a spectral analysis of the input audio signal so that the filter bank compression and/or the adaptation of the mapping scheme could be adjusted to the actual low bandwidth input audio signal.

In case that there are several audio signal input channels to the sound processor 24, as in the example of FIG. 1, which has three input channels, namely the microphone 20, the T-coil 56 and the wired input interface 58, the control unit 54 may control the sound processor 24 in such a manner that all input channels except for one are switched-off or are damped.

According to one example, in the low bandwidth operation mode the sampling frequency applied to the input audio signal may be reduced with regard to the sampling frequency used in the standard operation mode. Thereby, the frequency resolution may be increased or the FFT size may be decreased in order to save computational power.

In the low bandwidth operation mode, the frequency-gain function may be optimized to emphasize the most relevant spectral information for the signal, i.e., a gain function different to the gain function applied in the standard operation mode may be applied. For example, in the low bandwidth operation mode the threshold current levels ("T-levels") may be reduced compared to the standard operation mode, resulting in less current amplitudes for soft signals. Thus, the parameters of the amplitude compression may be optimized in order to amplify soft parts of the signal and to attenuate soft noise.

According to one example, a frequency transposition and/or a frequency expansion may be applied to the audio input signal prior to mapping of the analysis channels to the stimulation channels.

According to one example, the noise level in each analysis channel may be determined, and the stimulation signal may be set to zero for stimulation channels in which the noise level of the attributed analysis channel is above a certain threshold; thereby noise signals may be prevented from being perceived.

While the invention has been illustrated so far by reference to CI systems, the principles of the invention are equally applicable to other neural stimulation systems, such as an auditory brain stem implant or an auditory mid-brain implant.

Further, the invention also may be used not only with unilateral CIs, but also with bimodal systems (with a CI at one ear and a hearing aid at the other ear), bilateral systems (with one CI at each ear) and hybrid systems (a hearing aid and a CI on the same ear). In bimodal and bilateral systems the telephone signal may be streamed from one ear to the other ear, as it is known in the art.

If the device comprises an electro-acoustic hearing aid at the same ear as the auditory prosthesis or at the other ear, in the standard operation mode, signal components having frequencies below a threshold may be presented via the loudspeaker of the electro-acoustic hearing aid but not via the auditory prosthesis device, while signal components having frequencies above the threshold are presented via the auditory prosthesis device but not via the loudspeaker of the electro-acoustic hearing aid; in the low bandwidth operation mode signal also components having frequencies below the threshold may be presented via the auditory prosthesis device. For example, in a hybrid system frequencies up to 1000 Hz may be presented, and frequencies above 1000 Hz may be presented electrically. For bandlimited signals signal manipulations may be performed, e.g., the whole spectrum of the telephone signal may be applied to the electrodes.

What is claimed is:

1. An auditory prosthesis device for neural stimulation of a patient's hearing, comprising
    means for providing an input audio signal;
        a sound processor for generating a neural stimulation signal from the input audio signal; and
        an implantable stimulation assembly having a plurality of stimulation channels (52) for stimulation of the patient's hearing according to the neural stimulation signal, the implantable stimulation assembly being configured for implantation in the cochlear of a patient,
    the sound processor comprising a filterbank for dividing the input audio signal into a plurality of analysis channels, each containing a frequency domain signal representative of a distinct frequency portion of the audio signal, means for determining a signal level for each analysis channel by analyzing the respective frequency domain signal, means for generating a neural stimulation signal for each analysis channel according to the respective signal level, a mapping unit for allocating the analysis channels to the stimulation channels according to an adjustable mapping scheme, and a control unit for controlling the mapping unit such that a standard mapping scheme is used in a standard operation mode and a low bandwidth mapping scheme different to the standard mapping scheme is used in a low bandwidth operation mode in which the bandwidth of the input audio signal is lower than in the standard operation mode.

2. The device of claim 1, wherein in the low bandwidth mapping scheme at least one of the analysis channels is allocated to a stimulation channel corresponding to higher or lower frequency stimulation than the stimulation it is mapped to in the standard mapping scheme.

3. The device of claim 2, wherein in the low bandwidth mapping scheme the analysis channels having a center frequency above a threshold value are allocated to a stimulation channel corresponding to higher frequency stimulation than the stimulation channel the respective analysis channel is allocated to in the standard mapping scheme.

4. The device of claim 2, wherein in the low bandwidth mapping scheme the analysis channels having a center frequency below a threshold value are allocated to a stimulation channel corresponding to lower frequency stimulation than the stimulation channel the respective analysis channel is allocated to in the standard mapping scheme.

5. The device of claim 3, wherein in the low bandwidth mapping scheme the analysis channels having a center frequency above the upper limit or a lower limit of the input audio signal spectrum are no longer allocated to a stimulation channel.

6. The device of claim 1, wherein the sound processor is designed such that in the low bandwidth operation mode an artificial signal is reconstructed from the input audio signal, which artificial signal consists of frequencies outside the bandwidth of the input audio signal, wherein a stimulation signal is generated from the artificial signal which is supplied to a stimulation channel which is not allocated to an analysis channel in the low bandwidth operation mode.

7. An auditory prosthesis device for neural stimulation of a patient's hearing, comprising means for providing an input audio signal;
a sound processor for generating a neural stimulation signal from the input audio signal; and
an implantable stimulation assembly having a plurality of stimulation channels for stimulation of the patient's hearing according to the neural stimulation signal, the implantable stimulation assembly being configured for implantation in the cochlear of a patient, the sound processor comprising
an adjustable filterbank for dividing the input audio signal into a plurality of analysis channels each containing a frequency domain signal representative of a distinct frequency portion of the audio signal, means for determining a signal level for each analysis channel by analyzing the respective frequency domain signal, means for generating a neural stimulation signal for each analysis channel according to the respective signal level, a mapping unit for allocating the analysis channels to the stimulation channels and a control unit for controlling the filterbank such that in a standard operation mode a standard filterbank setting is used and in a low bandwidth operation mode in which the bandwidth of the input audio signal is lower than in the standard operation mode a low bandwidth filterbank setting is used which is different from the standard filterbank setting with regard to the center frequency and the width of at least part of the analysis channels.

8. The device of claim 7, wherein in the low bandwidth filterbank setting the filterbank is adapted towards lower frequencies with regard to the standard filterbank setting by lowering the center frequency and the width of at least some of the analysis channels.

9. The device of claim 8, wherein in the low bandwidth filterbank setting the center frequency of each analysis channel is lowered the more the higher the respective center frequency in the standard filterbank setting is.

10. The device of claim 8, wherein in the low bandwidth filterbank setting the filterbank is compressed to such an extent that the upper frequency limit of the low bandwidth input audio signal falls within that analysis channel having the highest frequency range.

11. The device of claim 7, wherein the control unit (54) is adapted to control the mapping unit (46) such that the mapping scheme is the same in both the standard operation mode and the low bandwidth operation mode.

12. The device claim 7, wherein the control unit (54) is adapted to control the mapping unit (46) such that a standard mapping scheme is used in the standard operation mode and a low bandwidth mapping scheme different to the standard mapping scheme is used in the low bandwidth operation mode.

13. The device of claim 1, further comprising a manually operable switch (64) for causing the control unit (54) to switch between the standard operation mode and the low bandwidth operation mode.

14. The device of claim 1, wherein the sound processor (24) comprising a classifier unit (44) for determining whether the input audio signal qualifies as a low bandwidth input audio signal having a bandwidth lower than a standard input audio signal, wherein the classifier unit is adapted to cause the control unit (54) to switch form the standard operation mode to the low bandwidth operation mode in case that a low bandwidth input audio signal is determined.

15. The device of claim 1, wherein the means for providing an input audio signal comprise at least one of the following input channels: a microphone arrangement, a receiver for wireless audio signal transmission, and an interface (58) for wired audio signal transmission.

16. The device of claim 15, wherein the sound processor is designed such that in the low bandwidth operation mode all input channels except for one are switched off or are damped.

17. The device of claim 1, wherein the sound processor comprises a noise reduction unit.

18. The device of claim 1, wherein the sound processor is designed such that in the low bandwidth operation mode a gain function is applied which is different to the gain function applied in the standard operation mode.

19. The device of claim 18, wherein the sound processor is designed such that in the low bandwidth operation mode the threshold current levels and/or the M-levels are changed, preferably reduced, compared to the standard operation mode.

20. The device of claim 1, wherein in the low bandwidth operation mode the sampling frequency applied to the input audio signal is reduced with regard to the sampling frequency of the standard operation mode.

21. The device of claim 1, wherein the sound processor comprises means for applying at least one of frequency transposition and frequency expansion to the audio input signal prior to mapping of the analysis channels to the stimulation channels.

22. The device of claim 1, wherein the sound processor comprises means for determining the noise level in each analysis channel, wherein the means for generating the neural stimulation signal are adapted to set the stimulation signal to zero for a stimulation channel to which an analysis channel is mapped in which the noise level is above a threshold.

23. The device of claim 1, wherein the neural stimulation signals are auditory nerve stimulation signals.

24. The device of claim 23, wherein the implantable stimulation assembly comprises a plurality of stimulation electrodes and wherein each stimulation channel is attributed to at least one of the stimulation electrodes.

25. A system comprising an auditory prosthesis device claim 1 to be worn at one ear of the patient and a hearing aid to be worn at the same ear or at the other ear of the patient.

26. The system of claim 25, wherein in the standard operation mode signal components having frequencies below a threshold are presented via the loudspeaker of the electro-acoustic hearing aid but not via the auditory prosthesis device, while signal components having frequencies above the threshold are presented via the auditory prosthesis device but not via the loudspeaker of the electro-acoustic hearing aid, whereas in the low bandwidth operation mode signal also components having frequencies below the threshold are presented via the auditory prosthesis device.

27. A system comprising a first auditory prosthesis devices of claim 1 to be worn at one ear of the patient and a second auditory prosthesis devices of claim 1 to be worn at the other ear of the patient.

28. A method of neural stimulation of a patient's hearing, comprising
providing an input audio signal;
dividing the input audio signal, by a filterbank into a plurality of analysis channels, each containing a frequency domain signal representative of a distinct frequency portion of the audio signal;
determining a signal level for each analysis channel by analyzing the respective frequency domain signal,
generating a neural stimulation signal for each analysis channel according to the respective signal level;
allocating the analysis channels to a plurality of stimulation channels of an implantable stimulation assembly located in the cochlear of a patient according to an adjustable mapping scheme,
stimulating, by the implantable stimulation assembly, the patient's hearing according to the neural stimulation signals applied to the stimulation assembly,
wherein a standard mapping scheme is used in a standard operation mode and a low bandwidth mapping scheme different to the standard mapping scheme is used in a low bandwidth operation mode in which the bandwidth of the input audio signal is lower than in the standard operation mode.

29. A method of neural stimulation of a patient's hearing, comprising
providing an input audio signal;
dividing the input audio signal, by a filterbank having an adjustable filterbank setting, into a plurality of analysis channels each containing a frequency domain signal representative of a distinct frequency portion of the audio signal;
determining a signal level for each analysis channel by analyzing the respective frequency domain signal,
generating a neural stimulation signal for each analysis channel according to the respective signal level;
allocating the analysis channels to a plurality of stimulation channels of an implantable stimulation assembly located in the cochlear of a patient according to a mapping scheme,
stimulating, by the implantable stimulation assembly, the patient's hearing according to the neural stimulation signals applied to the stimulation assembly,
wherein in a standard operation mode a standard filterbank setting is used and in a low bandwidth operation mode in which the bandwidth of the input audio signal is lower than in the standard operation mode a low bandwidth filterbank setting is used which is different from the standard filterbank setting with regard to the center frequency and the width of at least part of the analysis channels.

30. The method of claim 29, wherein the audio input signal in the low bandwidth operation mode is a telephone signal.

31. The method of claim 28, wherein the audio input signal in the low bandwidth operation mode is a telephone signal.

* * * * *